(12) United States Patent
Yu et al.

(10) Patent No.: US 11,439,338 B2
(45) Date of Patent: Sep. 13, 2022

(54) THREE-DIMENSIONAL SILICON-BASED COMB PROBE

(71) Applicant: International Business Machines Corporation, Armonk, NY (US)

(72) Inventors: Roy R. Yu, Poughkeepsie, NY (US); Emily R. Kinser, Poughkeepsie, NY (US); Hariklia Deligianni, Alpine, NJ (US)

(73) Assignee: International Business Machines Corporation, Armonk, NY (US)

( * ) Notice: Subject to any disclaimer, the term of this patent is extended or adjusted under 35 U.S.C. 154(b) by 717 days.

(21) Appl. No.: 16/204,703

(22) Filed: Nov. 29, 2018

(65) Prior Publication Data

US 2020/0170533 A1 Jun. 4, 2020

(51) Int. Cl.
*A61B 5/291* (2021.01)

(52) U.S. Cl.
CPC .................... *A61B 5/291* (2021.01)

(58) Field of Classification Search
CPC ......... A61B 5/25; A61B 5/686; A61B 5/6868; A61B 2562/046
See application file for complete search history.

(56) References Cited

U.S. PATENT DOCUMENTS

| 9,399,128 | B2 * | 7/2016 | Tooker | A61B 5/6867 |
| 10,161,898 | B2 * | 12/2018 | Kinser | C12Q 1/006 |
| 2004/0006264 | A1 * | 1/2004 | Mojarradi | A61B 5/291 600/378 |
| 2007/0007240 | A1 * | 1/2007 | Wise | H01L 24/24 156/247 |
| 2007/0265543 | A1 * | 11/2007 | VanSickle | A61B 5/4094 600/544 |
| 2010/0066346 | A1 * | 3/2010 | Zhang | C23C 28/322 324/71.1 |
| 2015/0128413 | A1 * | 5/2015 | Vetter | A61N 1/0529 29/854 |
| 2017/0112405 | A1 * | 4/2017 | Sterrett | A61B 5/287 |
| 2017/0209079 | A1 * | 7/2017 | Kinser | A61B 5/14532 |
| 2018/0078162 | A1 * | 3/2018 | Han | A61B 5/24 |

OTHER PUBLICATIONS

List of IBM Patents or Patent Applications Treated as Related pp. 1-2 Nov. 30, 2018.

(Continued)

*Primary Examiner* — Eun Hwa Kim
(74) *Attorney, Agent, or Firm* — L. Jeffrey Kelly; Otterstedt & Kammer PLLC (57) ABSTRACT

A three-dimensional (3D) comb probe structure includes a carrier, a plurality of combs arranged in the carrier and spaced apart from one another, a plurality of shanks forming the combs, each shank including a base portion and a stem portion extending from the base portion, wherein sets of the shanks are joined together by the base portions thereof to form a respective comb, and a plurality of sensing elements disposed along the stem portion of each of the shanks and electrically connected to electrical contacts disposed at respective ones of the base portions. The sensing elements can include nanopatterned features on surfaces thereof forming a non-random topography.

16 Claims, 5 Drawing Sheets

(56) References Cited

OTHER PUBLICATIONS

James J. Jun et al. Fully Integrated Silicon Probes for High-Density Recording of Neural Activity, Nature. Nov. 8, 2017; 551(7679): pp. 232-236. doi:10 1038/nature24636.
Charles W. Lu et al. Current Challenges to the Clinical Translation of Brain Machine Interface Technology, Chapter 7. International Review of Neurobiology, vol. 107, pp. 137-160, Nov. 2012, Elsevier Inc. ISSN 0074-7742.
Anonymous, A 3-D light switch for the brain, Nov. 19, 2012, Optical Society of America, pp. 1-3. Nov. 2012.
Rubehn B. Wolff, A Light Switch Inside the Brain, Bernstein Newsletter, Bernstein Network Computational Neuroscience, p. 6, Jun. 2013.

\* cited by examiner

THREE-DIMENSIONAL SILICON-BASED COMB PROBE

The present invention relates generally to sensors and more particular to three-dimensional (3D) silicon-based comb probes for neural sensing and stimulation, with the ability to perform both electrical and chemical sensing.

Sensing of neural activity provides significant insight into the functioning of brain state, which can help identify root causes of motor or sensory impairments that may impact individuals. Magnetic resonance imaging (MRI) is a common brain activity imaging technology, which provides a view of global brain function activity. By design MRI cannot provide the cell-to-cell networking details of brain cellular signaling, such as electrical activity of neurons. For millisecond time scale sensitivity to neural activity and the localization of cell action origin, an implant with cellular resolution is needed.

The utilization of neural probe technologies provides many benefits for medical care of individuals. Electrical brain stimulations and detection using implanted devices, for example, using a Spencer depth electrode probe, have clinical applications in deep brain implant target the thalamus region for epileptic seizure treatment, and more recently, for chronical depression treatment. At a targeted location (e.g., near the thalamus) the Spencer probe can detect the on-set of abnormal brain activity and deliver a pulse of electrical stimulation to either stop the abnormal brain activity or to initiate normal brain activity. Such a continuously monitoring-stimulating feedback loop can be effective for patients at risk for seizure. Similar techniques are used for chronical pain management with spinal cord implant. While recent improvements in neural probe technology feature reduced size, specifically with reduced electrode size, the density of electrodes on said probes limits the resolution for monitoring brain activity and offers limited precision for stimulation. The same challenges of resolution and precision are also associated with 2D devices applied to the top surface of the brain.

BRIEF SUMMARY

According to an embodiment of the present invention, a three-dimensional (3D) comb probe structure includes a carrier, a plurality of combs arranged in the carrier and spaced apart from one another, a plurality of shanks forming the combs, each shank including a base portion and a stem portion extending from the base portion, wherein sets of the shanks are joined together by the base portions thereof to form a respective comb, and a plurality of sensing elements disposed along the stem portion of each of the shanks and electrically connected to electrical contacts disposed at respective ones of the base portions. The sensing elements can include nanopatterned features on surfaces thereof forming a non-random topography.

According to an embodiment of the present invention, a comb structure includes a plurality of shanks disposed in a one-dimensional array, each of the shanks comprising a base portion and a stem portion, wherein the base portions of the shanks are sequentially connected, and a plurality of sensing elements formed on each of the stem portions.

According to an embodiment of the present invention, a shank structure includes a base portion, a stem portion, and a plurality of sensing elements formed on the stem portion, wherein the sensing elements are electrically connected to an input/output interface disposed in the base portion.

Features and techniques associated with the present invention can provide substantial beneficial technical effects. The features and advantages of the present invention will become apparent from the following detailed description of illustrative embodiments thereof, which is to be read in connection with the accompanying drawings.

BRIEF DESCRIPTION OF THE DRAWINGS

Preferred embodiments of the present invention will be described below in more detail, with reference to the accompanying drawings.

DETAILED DESCRIPTION

For the sake of brevity, conventional techniques related to semiconductor fabrication may or may not be described in detail herein. Moreover, the various tasks and process steps described herein can be incorporated into a more comprehensive procedure or process having additional steps or functionality not described in detail herein. In particular, various steps in the manufacture of semiconductors are well-known and so, in the interest of brevity, conventional steps may be mentioned briefly herein or will be omitted entirely without providing the process details known to those skilled in art.

Turning now to an overview of technologies that are more specifically relevant to aspects of the invention, while recent improvements in neural probes have reduced the electrode size, the electrodes associated with commercially available devices are cumbersome in size, and such devices feature only a small number of electrode contacts per device, e.g., less than 20 electrode contacts. While useful for bulk stimulations and limited electrical sensing, commercially available devices also do not include a high enough density of electrodes to be useful in quantifying and understanding the behavior of individual cells. Moreover, the surface-based electrode grids only interact with and measure electrical signals from the top surface of the brain, as the electrodes only contact this surface. Therefore, it is not possible to accurately measure the electrical properties of a 3D region of the brain. While the incorporation of silicon-based semiconductor manufacturing techniques enable fabrication of millions of electrode sensor structures, these electrode sensor structures are traditionally limited to 2D monitoring due to the planar nature of silicon substrates and the associated processing techniques. Additionally, incorporating dense electrode arrays creates challenges relating to wiring out the electrodes to link to external systems for processing the acquired data and communicating signals related to stimulation procedures.

Turning now to an overview of the aspects of the invention, one or more embodiments of the invention address these and other challenges by providing an implantable 3D comb probe sensor unit for monitoring and stimulation of tissue (e.g., brain tissue).

One or more embodiments of the present invention include a 3D comb probe sensor unit having improved integration and interaction in 3D spaces, specifically providing direct interface with cognitive cortex areas.

In some embodiments the 3D comb probe sensor unit enables the application and sensing (read and write) of electrical signals in tissue. According to one or more embodiments, the sensor units coordinates processing of signals to/from multiple sensors and/or comb probe structures (e.g., between cortex and the thalamus activity).

According to an exemplary embodiment of the present invention, both chemical and electrical sensing modes may be incorporated into the 3D comb probe sensor unit. Structures associated with the 3D comb probe sensor unit described herein are adaptable to different types of implants and probe types (e.g., Spencer probe).

Embodiments of the present invention include methods and systems of interconnecting a large number (e.g., millions) of sensing units in a small three-dimensional volume (e.g., less than about 1 centimeter cubed ($cm^3$)). Some embodiments of the present invention use a method referred to those skilled in the art as "4DI" semiconductor fabrication methodology. Semiconductor device technology design nodes commonly referred to as 7 nanometers (nm), 14 nm, 20 nm, and 22 nm nodes may be utilized to manufacture a 3D comb probe sensor unit according to embodiments of the present invention.

Embodiments of the present invention are related to a 3D comb probe sensor unit (hereinafter 3D comb probe) and more particular to a 3D comb probe for brain (and more particularly cortex) stimulation and detection, and a method for manufacturing the same. Exemplary implementations of the comb probe sensor device include direct interactions with areas of the brain associated with sensory, motor, vision, and speech functions, without the need for sensors interacting with peripheral neural networks.

Figure 1:
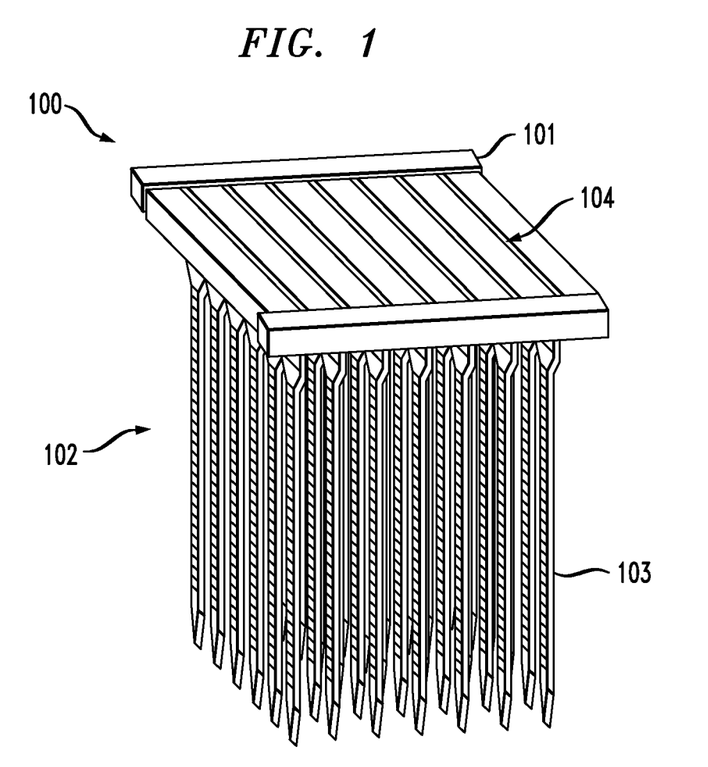
FIG. 1 depicts a schematic illustration of an exemplary silicon-based 3D comb probe according to an embodiment of the present invention.

FIG. 1 depicts an exemplary 3D comb probe 100 according to an embodiment of the present invention. The 3D comb probe 100 comprises a carrier 101 bearing a plurality of combs, e.g., 102, each of the combs comprising a plurality of shanks, e.g., 103. Each shank includes a plurality of sensing elements (see FIGS. 2 and 3). The combs are arranged in carrier 101 such that the plurality of shanks extend in slots 104 such that the shanks are arranged substantially perpendicular to the carrier 101 in order to create a three-dimensional sensor structure. In some embodiments a control chip (not shown) is connected to top portions of the combs, for example, by solder bumps.

Figure 2:
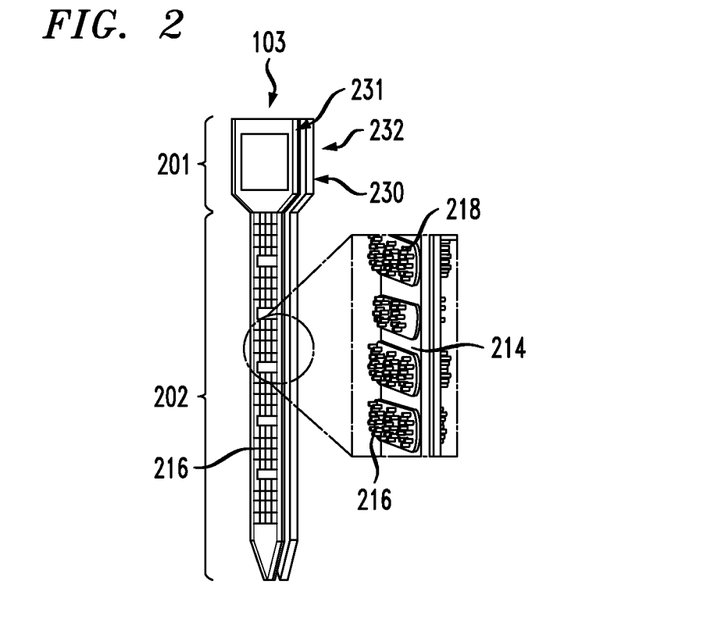
FIG. 2 depicts a schematic illustration of an exemplary shank associated with a comb structure of the 3D comb probe according to an embodiment of the present invention.

FIG. 2 depicts an exemplary shank 103 according to an embodiment of the present invention. The shank 103 includes a probe base 201 and a probe stem 202. The length of the shank 103, specifically the length of probe stem 202, in each comb 300 is designed to be inserted into the cortex of the brain such that the shank 103 can interact with the neurons throughout the various layers of cortex. In some embodiments, dimensions of the probe base 201 are designed to be inserted and secured in a slot (e.g., 104) in the carrier 101. In at least one exemplary embodiment the probe base 201 has dimensions of about 300 um by 300 um in horizontal cross section, and is about 3-5 mm in length (i.e., along an entire length of the shank 103), and preferably about 3 mm long.

According to at least one exemplary embodiment, the length of the probe base 201 depends on a number of driving circuits embedded therein. According to at least one exemplary embodiment, for implementations with few circuits, the probe base 201 is small, e.g., about 500 um in length. In view of the foregoing, the probe base 201 can be formed having a height in the range of about 0.5 mm and 5 mm. The probe stem 202 has a horizontal cross-sectional thickness measuring between about 50-100 um, and having a length (i.e., along an entire length of the shank 103) between about 2 mm and 10 mm.

According to some embodiments, each of the shanks, e.g., 103, includes sensing elements disposed on one or more sides of the probe stem 202. For example, the shanks can be formed having sensors disposed on only one surface in a single sided configuration or on more than one surface, e.g., in a double sided configuration with sensors disposed on two surfaces of the shanks, as illustrated in FIG. 2. According to one or more embodiments of the present invention, the probe stems 202 include feature sensing elements 216 on one or both sides of the exposed shank.

In some embodiments, each shank, e.g., 103, is double sided with sensing elements 216 arranged on a first side 231 (a front side or first sub-shank) and a second side 232 (a back side or a second sub-shank). In an additional embodiment, shank 103 may feature sensing elements arranged on only one side of a shank. In the case of a double sided shank structure, the first side 231 and the second side 232 of each shank includes a substrate 402 (see FIG. 4) onto which a plurality of sensing elements 216 are formed.

Figure 4:
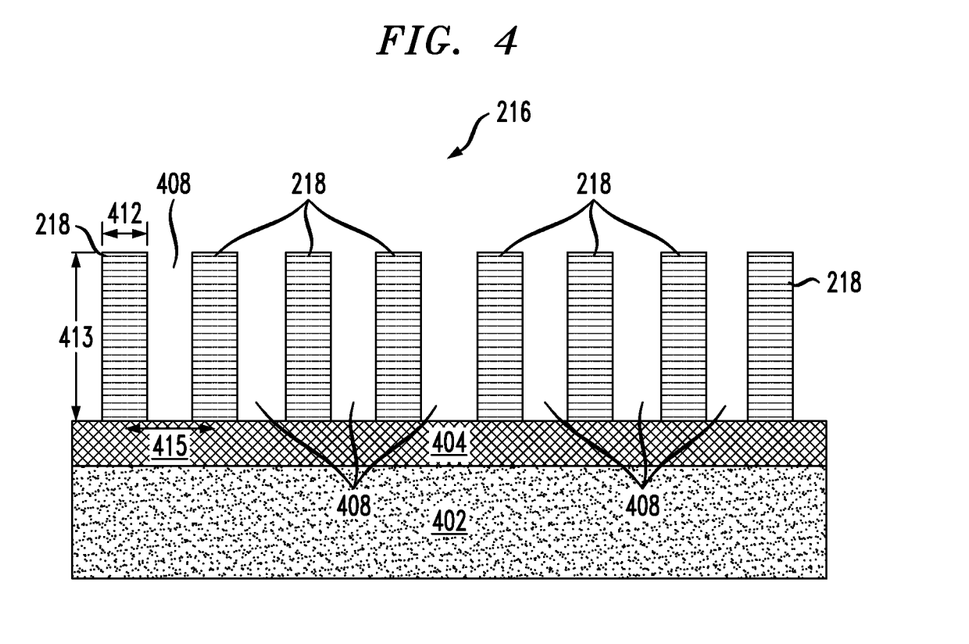
FIG. 4 depicts a cross-sectional side view of a sensing element with nano-features according to embodiments of the present invention.

The substrate 402 may be comprised of a semiconductor substrate, a polymeric material, a biocompatible material, etc. In some embodiments the sensing elements 216 on the first side 231 and the second side 232 are separated by spacing 214 (see FIG. 2) ensuring that sensing elements 216 function as individual sensors. According to at least one embodiment, the spacing 214 comprises a dielectric material. In some embodiments the first side 231 and the second side 232 are separately formed and joined together, with non-patterned faces of the first side 231 and the second side 232 aligned face-to-face, exposing the faces of shank 103 with sensing elements to an outside, and configured to contact tissue. According to at least one embodiment of the present invention, the first side 231 and the second side 232 of shank 200 are joined by a bonding layer 230. In some embodiments the bonding layer 230 is an adhesive, a ceramic-ceramic bond, a metal-metal bond, a Teflon polymer, etc. According to at least on embodiment, the adhesive 230 is a polyimide adhesive As also depicted in FIG. 2, each sensing element 216 on the surfaces of the shanks 202 includes nano-patterned features 218. In some embodiments, the nano-patterned features 218 serve as a component to reduce tissue injury response and accelerate tissue repair after insertion and promoting interaction of neurons with the sensing element surfaces. Using appropriately sized nano-patterned features 218 reduces microglial activation and antibody responses. The nano-patterned features 218 also enhance neural signal and signal quality during sensing due to the increased surface area of sensing elements 216. Additionally, the nanopatterned features improve stimulation of targeted portions of the brain. According to at least one embodiments of the present invention, the nano-patterned features 218 increase a total surface area of sensing elements 216 by factor of about 2 to 10 times. For example, a critical diameter and height of the nanorod structures increases the local electrical field, thereby increasing the sensitivity of the sensing element 216 compared with a flat sensing element surface.

FIG. 4 depicts a cross-sectional side view of a sensing element 216 with nanopatterned features 218 according to embodiments of the present invention. Each sensing element 216 is formed on a substrate 402 that includes a semiconductor material. A base layer 404 is formed on the substrate 402, and nanopatterned features 218 are formed on the base layer 404. In a preferred embodiment, base layer 404 functions as an electrode.

Located on the exposed surface of base layer 404, the nano-patterned features 218 form a non-random topography on a surface of the base layer 404. The nano-patterned features 218 are an array of non-random (i.e., regular repeating) repeating individually articulated features formed on the base layer 404. The repeating individually articulated features can have various shapes and sizes. Non-limiting examples of shapes for each repeating individually articulated features include rods, cones, annular structures (e.g., hollow tubes), or any combination thereof.

In one or more embodiments of the present invention, the nano-patterned features 218 have a critical dimension 412, i.e., diameter or width, from about 5 nm to about 600 nm. In other embodiments of the present invention, the nano-patterned features 218 have a critical dimension from about 20 nm to about 300 nm. In some embodiments of the present invention, the nano-patterned features 218 have a height 413 from about 5 nm to about 20 micrometers (μm). In one or more embodiments of the present invention, each of nano-patterned features 218 has an aspect ratio (i.e., ratio of width to height) of from about 1:1 to about 50:1. In other embodiments of the present invention, each of nano-patterned features 218 has a pitch 415 of from about 2:1 to 20:1. Pitch 415 refers to the center-to-center distance of nearest-neighbor features.

The nano-patterned features 218 include one or more conductive material(s). The conductive material forming the nano-patterned features 218 can be the same as the conductive material forming the base layer 404 according to some embodiments of the present invention. Yet, in other embodiments of the present invention, the conductive material forming the nano-patterned features 218 is different than the conductive material forming the base layer 404. The conductive material forming the nano-patterned features 218 can include a metallic material, including an alloy of more than one metal. The conductive material can include an alloy of metallic components, or an alloy of metallic and non-metallic components. The conductive material can include, but is not limited to, platinum, copper, silver, gold, tungsten, aluminum, iron, palladium, nickel, titanium, zirconium, phosphorus, carbon, or a combination thereof. In one or more embodiments of the present invention, the conductive material is in a crystalline state. In other embodiments of the present invention, the conductive material is in an amorphous state.

Depending on the materials used for the nano-patterned features 218, various methods can be used to form the nano-patterned features 218. According to some embodiments of the present invention, the nano-patterned features 218 are formed using direct electroplating. Yet, in other embodiments of the present invention, the material forming the nano-patterned features 218 can be overgrown and subsequently etched back or polished to the desired size/shape/dimension. Photolithography, etching, and chemical mechanical planarization (referred to as CMP), are other non-limiting examples of methods that can be used to form the nano-patterned features 218 on the surface of the base layer 404.

According to some embodiments, the nanorods are formed of a gold base nanorod structure with a platinum coating in order to increase bio-compatibility and enable oxygen sensing in cellular enzymatic redox reaction.

According to one or more embodiments of the present invention, the sensing elements 216 function as electrical sensors or chemical sensors. In the exemplary case of chemical sensors, an enzyme specific to the chemical of interest (e.g., glutamate, dopamine) may be functionalized onto all or part of the sensing surface of sensing element 216.

According to one or more exemplary embodiments of the present invention, embedded devices (not shown) are disposed in the shanks, e.g., under the sensing elements 216, and electrically connected to the base layer 402 of sensing elements. For example, the embedded devices can include active logic, memory, multiplexers, etc., which are embedded in the shanks, and/or are disposed in a control chip (see for example, control chip 614, FIG. 6E). In some embodiments, the circuits of the shank include front-end-of-line (FEOL) devices, back-end-of-line (BEOL) interconnects and sensing elements.

According to at least one exemplary embodiment, the probe base 201 associated with a shank 103 includes an embedded device, such as a memory device. As shown in FIG. 1, the probe base 201 is fixed in a gap 104 formed in the carrier 101, such that the carrier holds a shank and/or a comb of shanks in a fixed position.

According to at least one exemplary embodiment and referring again to FIG. 1, the 3D comb probe 100 has an area of about 10 mm by 10 mm (length and width), with each shank, e.g., 103, having a probe stem having a length between about 2 mm and 10 mm long (e.g., such that the 3D comb probe 100 has a height of approximately 10 mm). According to at least one exemplary embodiment, the shanks are disposed having a pitch of about 300 um. In an exemplary embodiment wherein each shank includes sensing elements disposed on an outer surface thereof and arranged in 2 to 5 columns disposed along a width of the shank, resulting in a total of 200 to 500 rows of sensing elements disposed along a length of the shank.

In some embodiments a shank includes 2 columns of sensing elements, each column having 500 sensing elements, disposed at 20 um pitch. In some embodiments a shank includes 4 columns of sensing elements, each column having 1000 sensing elements disposed at 10 um pitch. According to an exemplary embodiment of the present invention a 3D comb probe 100 is so constructed includes over 1,000,000 sensing elements.

According to one or more exemplary embodiments of the present invention, the sensing elements can be uni-polar or bi-polar; uni-polar sensors include one pad per sensing element, and bi-polar sensors include two pads per sensing elements.

According to one or more embodiments of the present invention, the 3D comb probe is are disposed on a top surface of the cortex and in contact with the brain cells. For an implementation with probe stems having a width of 100 um and a length of 10 mm, and with individual sensors measuring 10 um by 10 um in area and having a 20 um space between them, five rows of sensors width-wise aligned on the probe stem (see 202, FIG. 2), can be disposed on a given 3D comb probe. Again, given the probe stem 10 mm long, each column of sensors can be up to 10 mm long and include up to 500 sensors. In view of the foregoing, the exemplary probe stem can support 5×500=2500 sensors. Since a 10 um by 10 um area is needed for uni-polar sensor, there can be 2500 uni-polar sensors per probe stem. In the exemplary case of bi-polar sensors, there are two areas needed for each sensor, such that the exemplary probe stem can support up to 1250 bi-polar sensors.

Figure 3:
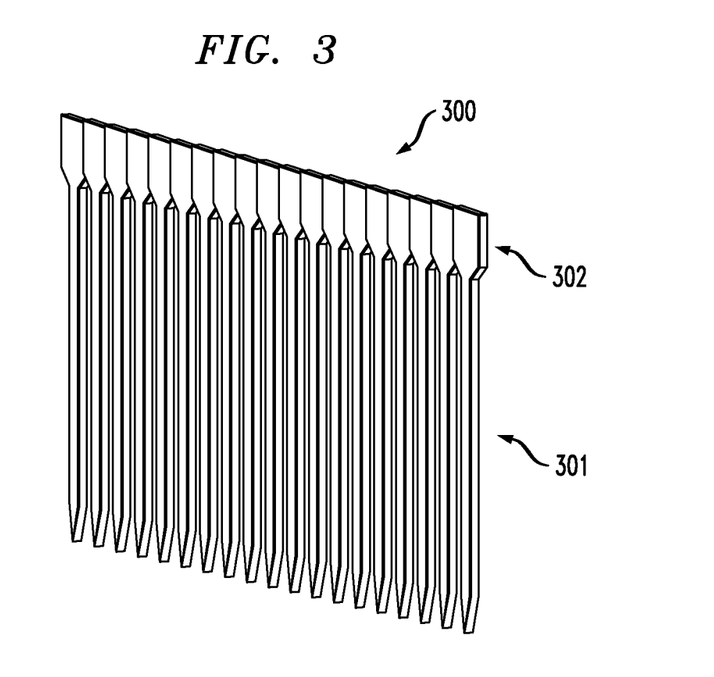
FIG. 3 depicts a schematic illustration of an exemplary comb structure comprising shanks according to an embodiment of the present invention.

According to at least one exemplary embodiment, the shanks are patterned from a semiconductor wafer substrate as individual components to be bonded into a comb or patterned from a wafer as a unitary comb 300 comprising a plurality of shanks 301 connected by the probe base portions 302 of the shanks (see FIG. 3). It should be understood that different combs can have different numbers of shanks. In some embodiments, a 3D comb probe includes an array of combs 300 (see also FIG. 1), with each comb including thirty-four or more shanks. In the exemplary case of a deep brain Spencer depth electrode probe where the number of shanks can be either 1, 2, or a few, with widths of about 2 mm and lengths up to 19 centimeters (cm) or more, a plurality of sensors (e.g., hundreds) can be disposed along the Spencer depth electrode probe length.

According to one or more exemplary embodiments of the present invention, input/output (I/O) for the combs is communicated through a top edge of the comb (i.e., a top edge of the base portions of the shanks) with fan-out wiring and micro-solder bumps disposed on the top edge. According to at least one exemplary embodiment of the present invention, a control logic chip is micro-soldered to the top edge of the comb (see FIGS. 6D and 6E).

It should be understood that the 3D comb probe 100, shanks 103, combs 102 etc., can be manufactured having different configurations (e.g., for surface 3D comb probes, deep probes, etc.) and that specific embodiments described herein are merely exemplary.

Figure 5:
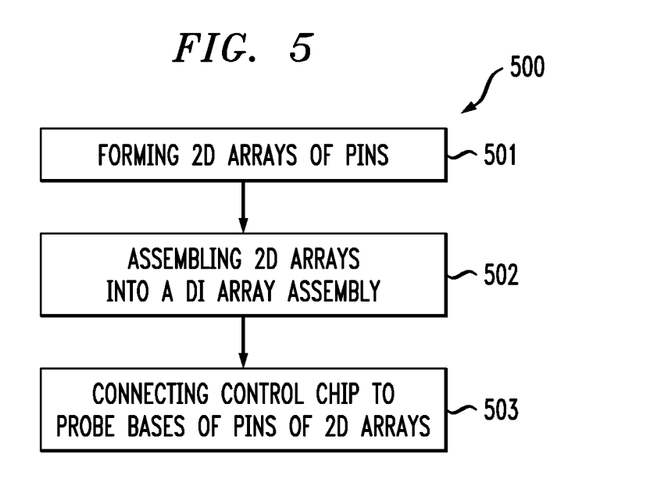
FIG. 5 depicts a flow diagram of a method of manufacturing a 3D comb probe sensor unit according to an embodiment of the present invention.

FIG. 5 depicts a method 500 of manufacturing the 3D comb probe 100 according to at least one exemplary embodiment of the present invention. The method includes forming a plurality of two-dimensional (2D) arrays of shanks (e.g., by patterning a silicon wafer) 501, assembling the plurality of 2D arrays into an array assembly (e.g., by bonding the 2D arrays into a 3-dimensional (3D) array, by inserting the 2D arrays into a platform, etc.) 502, and connecting a control chip to the probe bases of the 2D arrays 503.

Using a 4DI methodology, interconnects can be formed with micro-bump solder at 20 um pitch between the control chip and an edge surface of the comb array 300. Further interconnects can be formed of micro-bump solder at 20 um pitch between the carrier 101 and the comb 102. The carrier 101 is configured to secure the combs at a desired spacing (e.g., 300 um between the combs in a case of 100 um thick combs). In some embodiments the carrier 101 includes build-in circuitry, such as DRAM memory or non-volatile memory, which works with logic circuits in the probe base. According to at least one embodiment, the carrier 101 and combs 102 are joined together with 20 um pitch micro-solder bumps.

Figure 6A:
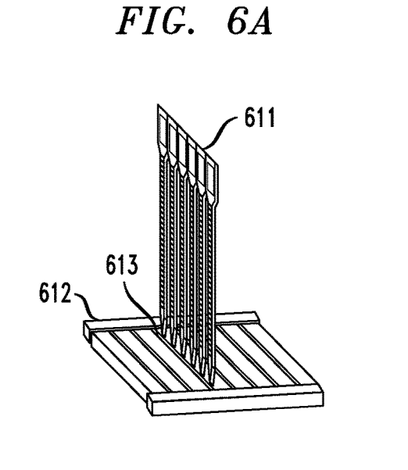
FIGS. 6A-6E depicts a method of manufacturing a 3D comb probe sensor unit described in FIGS. 1 and 4 according to an embodiment of the present invention.
Figure 6B:
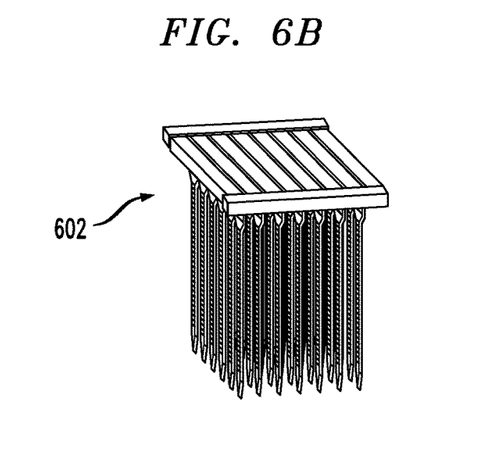
Figure 6C:
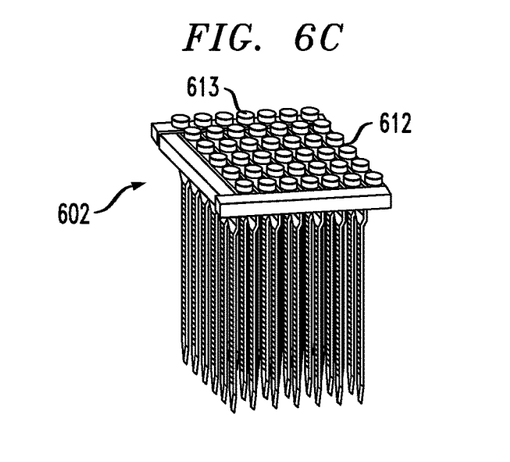
Figure 6D:
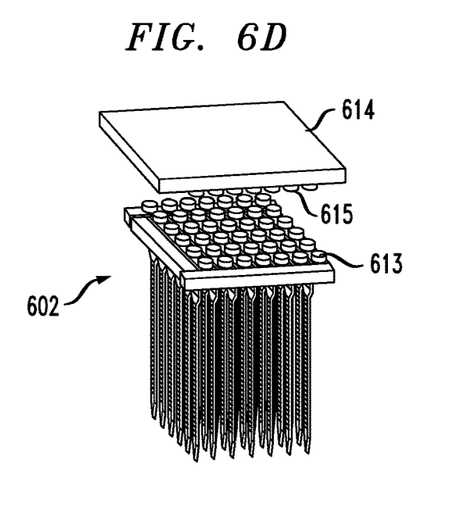
Figure 6E:
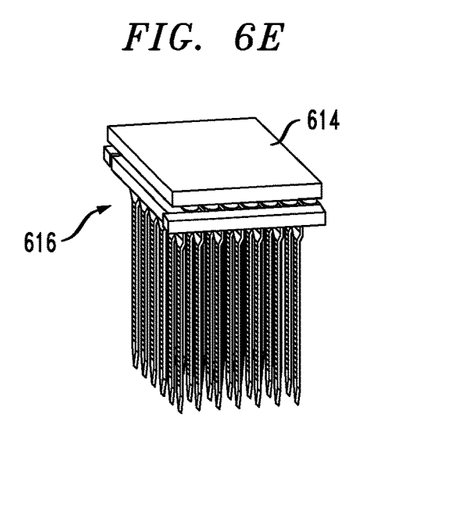

FIGS. 6A-6E depict a method of manufacturing a 3D comb probe, illustrating the method of FIG. 5. An exemplary carrier 612 is shown in FIG. 6A. The method includes disposing a plurality of combs, e.g., 611, in respective slots, e.g., 613, of the carrier 612 to form a lower assembly 602, which is illustrated in FIG. 6B. Moving to FIG. 6C, solder bumps 613 are formed on the top exposed surface on the lower assembly 602. The solder bumps 613 are bonded to contacts areas or pads of the lower assembly 602, and therefore solder bumps 613 can be formed on the top exposed surfaces of combs (e.g., exposed through the slots) and/or a top surface of the carrier 612. As illustrated in FIG. 6D, in some embodiments, a control chip 614 having solder bumps 615 on a bottom exposed surface thereof is bonded to the lower assembly 602. The control chip 614 and lower assembly 602 can be joined by re-flowing the solder bumps (613, 615), thermal compression bonding, or other methods known to those skilled in the art to form a 3D comb probe 616 (see FIG. 6E). The control chip 614 comprises an input/output interface (e.g., a wireless connectivity device) and a battery (not shown). According to at least one exemplary embodiment, the input/output interface includes a wireless charging coil for charging the battery.

According to exemplary embodiments of the present invention, the combs are stacked with about 300 um spacing between adjacent combs to form an array comprising 34×34=1156 shanks. According to exemplary embodiments of the present invention, the stacked 3D comb probe structure comprises 2500 sensing elements per shank, and comb structures 300 with an array of 1156 shanks, the stacked 3D comb probe structure comprising 2,890,000 sensing elements for single sided shanks, and 5,780,000 sensing elements for double sided shanks.

According to exemplary embodiments of the present invention, each shank has multi-layer wiring (e.g., 25 nm in pitch (4000 per layer)) connecting sensing elements 216 to respective probe base portions 201, where the probe base portions further comprise respective I/O processor and memory devices. In one or more exemplary embodiments of the present invention, the probe base portions have a size of about 300 um by 5 mm in area. I/O signals at each base portion are multiplex to a top surface of a respective shank top for electrical connection to a logic chip and system controller.

Turning again to the exemplary 3D comb probe 100, according to at least one embodiment of the present invention the carrier 103 can be formed by conventional semiconductor patterning techniques, including but not limited to photolithographic techniques.

According to one or more embodiments of the present invention, transistor devices are formed interconnected with wiring in the carrier 101 to form specific circuits with required functions logic, memory, multiplexing, waveform generation, etc. Due to limitations in the surface area (i.e., the size of 3D comb probe 100) and large number of sensors, 45 nm node and smaller semiconductor processes can be used, and more particularly, 5 nm to 22 nm node technology. In one exemplary embodiment, in the case of 22 nm node technology, 50 nm pitch interconnects can be fabricated. Stated generally, an exemplary stem portion is constructed using FEOL and BEOL constructions for interconnections and embedded devices, with sensor pads disposed on the stem portion using semiconductor fabrication methods known to those skilled in the art.

In some embodiments, the structure of a shank in cross section includes devices, interconnects, and sensors pads stacked on a surface of the stem portion. In some embodiments, devices (e.g., logic and memory) are constructed by FEOL processes and interconnects are constructed by BEOL processes with 22 nm silicon technology. According to exemplary embodiments of the present invention, the devices or local circuits under the sensors perform sensing functions avoiding I/O delay, and multiplex data to and from each sensing element. In one or more exemplary embodiments of the present invention, the sensing elements are arranged in a 5×10 block for I/O multiplexing. According to one or more embodiments, the sensing elements pads are disposed on one top layer, contacting the brain tissue after implantation.

Figure 7:
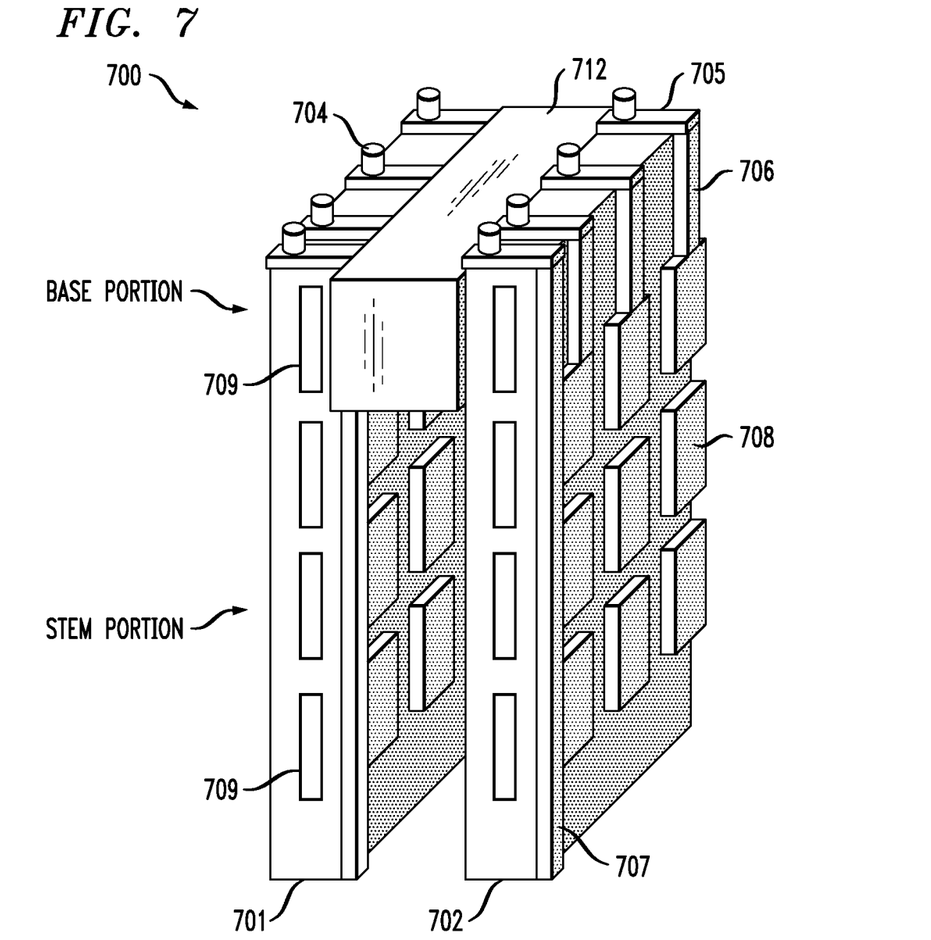
FIG. 7 is a schematic illustration of an exemplary digital input (DI) assembly associated with the interface of the carrier structure populated with comb structures to a control chip according to an embodiment of the present invention.

Referring to FIG. 7, a portion of an exemplary array assembly 700 is shown including two shanks 701 and 702, each having a base portion and a stem portion. A control chip (not shown) is bonded to an upper surface of the array assembly 700 by micro solder bumps, e.g., 704, disposed on, and electrically connected to, upper horizontal crossbars 705 which consist of electrically conductive material. In one or more exemplary embodiments of the present invention, the micro solder bumps 704 are deposed on a top edge of the shanks 701 and 702 having a pitch of about 10-20 um and fan-out wires 5 um in spacing (2000 edge fan-outs per layer per 10 mm comb width). Vertical crossbars 706 are electrically connected to embedded devices 709 (e.g., second memory, processors, and/or logic modules) disposed in the shanks and to sensing elements e.g., 708, disposed on a surface of the shanks. In some embodiments global I/O connectors 707 are connected to lower horizontal crossbars (not shown). In some embodiments, adjacent shanks 701 and 702 are arranged in the carrier 712, and can be bonded thereto using, for example, an adhesive.

According to at least one exemplary embodiment of the present invention, the control chip (not shown) can be electrically connected to the array assembly 700, i.e., over the base portions of the shanks. According to at least one embodiment of the present invention, the control chip comprises devices (e.g., first memory and/or logic modules), input/output (I/O) pads, etc.

Some exemplary implementations of embodiments described herein make use of direct 3D constructions with through silicon via (TSV) and micro-bump connections (area connections) for stacked stem controllers, logic devices, etc. (see FIGS. 6D-E and FIG. 7). Some embodiments include direct logic to a wireless transmitter for external I/O.

Given exemplary embodiments described herein, array assembly can achieve a data rate of about 100 Hz per sensing element, with 100 Hz×2000 sensing elements=20 kHz per stem, and 20 kHz×1000 stems=20 MHz per device. For example, with each Hz=8 bits (256 grey scale), a total data rate of 20 MB (160 Mb) one way or 40 MB bi-directional can be achieved. According to at least one exemplary embodiment, the array assembly includes a cache configured for 100 MB/s performance to hold and transfer data to logic and external for analysis.

According to exemplary embodiments of the present invention, sensors are disposed in 10 um pitch grids on the surfaces of the shanks 104 and the shanks comprise circuits (e.g., drivers, logic, memory) under the sensing elements, with I/O wiring electrically connecting the sensing elements to the shank base 201 and control chip 614 (see FIG. 6D). In one or more exemplary embodiments of the present invention, the shanks are lined in an array with spacing between the shanks of about 100 um to 500 um, and more preferably 300 um, the array forming a comb (e.g., see 300, FIG. 3) having a width (i.e., along the array of shanks) of about 10 mm.

According to exemplary embodiments of the present invention, a configuration of the shanks is selected depending on brain injury tolerance and recovery level.

Recapitulation:

According to an embodiment of the present invention, a three-dimensional stacked 3D comb probe structure (100) includes a carrier (101), a plurality of combs (102) arranged in the carrier and spaced apart from one another, a plurality of shanks (103) forming the combs, each shank comprising a base portion (201) and a stem portion (202) extending from the base portion, wherein sets of the shanks are joined together by the base portions thereof to form a respective comb (300), and a plurality of sensing elements (216) disposed along the stem portion of each of the shanks and electrically connected to electrical contacts disposed at respective ones of the base portions.

According to one or more embodiments of the present invention, neural signals detected by a 3D comb probe is analyzed by an external computer, which interprets the neural activity without the need for patient to describe thoughts or feelings.

According to one or more embodiments of the present invention, the 3D comb probe outputs electrical stimulus to the cortex and functions as motor implant, inducing movement in a patient.

According to one or more embodiments of the present invention, output from multiple implants are analyzed simultaneously. According to at least one embodiment of the present invention, the multiple implants include a 3D comb probe and a Spencer probe, to provide electrical and/or chemical sensing of the cortex and deep brain tissue, such that signals to and from the cortex and the thalamus are coordinated.

The illustrations of embodiments described herein are intended to provide a general understanding of the various embodiments, and they are not intended to serve as a complete description of all the elements and features of apparatus and systems that might make use of the assemblies and techniques described herein. Many other embodiments will become apparent to those skilled in the art given the teachings herein; other embodiments are utilized and derived therefrom, such that structural and logical substitutions and changes can be made without departing from the scope of this disclosure. It should also be noted that, in some alternative implementations, some of the steps of the exemplary methods may occur out of the order noted in the specification and/or figures. For example, two steps shown in succession may, in fact, be executed substantially concurrently, or certain steps may sometimes be executed in the reverse order, depending upon the functionality involved. The drawings are also merely representational and are not drawn to scale. Accordingly, the specification and drawings are to be regarded in an illustrative rather than a restrictive sense.

Embodiments are referred to herein, individually and/or collectively, by the term "embodiment" merely for convenience and without intending to limit the scope of this application to any single embodiment or inventive concept if more than one is, in fact, shown. Thus, although specific embodiments have been illustrated and described herein, it should be understood that an arrangement achieving the same purpose can be substituted for the specific embodiment(s) shown; that is, this disclosure is intended to cover any and all adaptations or variations of various embodiments. Combinations of the above embodiments, and other embodiments not specifically described herein, will become apparent to those of skill in the art given the teachings herein.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. Terms such as "above" and "below" are used to indicate relative positioning of elements or structures to each other as opposed to relative elevation.

The corresponding structures, materials, acts, and equivalents of any means or step-plus-function elements in the claims below are intended to include any structure, material, or act for performing the function in combination with other claimed elements as specifically claimed. The description of the various embodiments has been presented for purposes of illustration and description, but is not intended to be exhaustive or limited to the forms disclosed. Many modifications and variations will be apparent to those of ordinary skill in the art without departing from the scope and spirit thereof. The embodiments were chosen and described in order to best explain principles and practical applications, and to enable others of ordinary skill in the art to understand the various embodiments with various modifications as are suited to the particular use contemplated.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

The abstract is provided to comply with 37 C.F.R. § 1.72(b), which requires an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the appended claims reflect, the claimed subject matter may lie in less than all features of a single embodiment. Thus, the following claims are hereby incorporated into the Detailed Description, with each claim standing on its own as separately claimed subject matter.

Given the teachings provided herein, one of ordinary skill in the art will be able to contemplate other implementations and applications of the techniques and disclosed embodiments. Although illustrative embodiments have been described herein with reference to the accompanying drawings, it is to be understood that illustrative embodiments are not limited to those precise embodiments, and that various other changes and modifications are made therein by one skilled in the art without departing from the scope of the appended claims.

What is claimed is:

1. A three-dimensional (3D) comb probe structure comprising:
    a carrier;
    a plurality of combs arranged in the carrier and spaced apart from one another;
    a plurality of shanks forming each comb of the plurality of combs, each shank of the plurality of shanks comprising a base portion and a stem portion extending from the base portion, a plurality of upper horizontal crossbars disposed on an upper surface of the base portion, and a plurality of vertical crossbars disposed on a surface of the stem portion and electrically connected to the plurality of upper horizontal crossbars, wherein the upper surface of the base portion is perpendicular to the surface of the stem portion and wherein a set of the plurality of shanks are joined together at the base portions thereof to form a respective one of the plurality of combs;
    a plurality of sensing elements disposed along the stem portion of each of the shanks and electrically connected to the plurality of vertical crossbars;
    a control chip disposed on the carrier and directly, electrically, connected to the plurality of upper horizontal crossbars, wherein the control chip is disposed parallel to the upper surface of the base portion; and
    a solder bump on each upper horizontal crossbar of the plurality of upper horizontal crossbars, wherein the solder bumps form an array directly, electrically, connecting the control chip to each shank of the plurality of shanks forming each comb of the plurality of combs.

2. The 3D comb probe structure of claim 1, wherein each sensing element of the plurality of sensing elements comprises:
    a substrate that includes a semiconductor material; and
    a base layer, formed of a conductive material, formed on the substrate and bearing a plurality of nano-patterned features increasing a surface area of the base layer of the sensing element.

3. The 3D comb probe structure of claim 2, wherein the nano-patterned features are arranged in a non-random topography comprising repeating individually articulated features.

4. The 3D comb probe structure of claim 1, wherein each comb of the plurality of combs is formed of a set of the plurality of shanks disposed in a one-dimensional array.

5. The 3D comb probe structure of claim 1, wherein the carrier is configured to secure a number of the plurality of combs equal to a number of the plurality of shanks in each comb, such that the plurality of shanks of each comb are disposed in a two-dimensional array.

6. The 3D comb probe structure of claim 1, wherein the plurality of sensing elements disposed along the stem portions of the plurality of shanks are arranged in a three-dimensional array.

7. The 3D comb probe structure of claim 1, wherein the plurality of shanks are formed of silicon.

8. The 3D comb probe structure of claim 1, wherein the plurality of sensing elements are formed on a single side of the stem portions.

9. The 3D comb probe structure of claim 1, wherein the plurality of sensing elements are formed on opposite sides of the stem portions.

10. The 3D comb probe structure of claim 1, wherein each shank of the plurality of shanks is formed of two identical sub-shanks, and each of the two sub-shanks comprises a patterned face including a respective set of the plurality of sensing elements and a non-patterned face, wherein the non-patterned faces of two sub-shanks are bonded directly together by an adhesive, such that the plurality of sensing elements are formed on exposed faces of the sub-shanks and a first exposed face of the exposed faces forms the surface of the stem portion and a second exposed face of the exposed faces forms an opposite surface of the stem portion.

11. A shank structure comprising:
 a base portion;
 a stem portion;
 a plurality of sensing elements formed on a surface the stem portion; and
 an input/output interface on a top surface of the base portion, wherein an upper surface of the base portion is perpendicular to the surface of the stem portion, the input/output interface comprising a plurality of upper horizontal crossbars and a solder bump on each upper horizontal crossbar of the plurality of upper horizontal crossbars, wherein the plurality of sensing elements are electrically connected to the input/output interface disposed on the top surface of the base portion by an interconnect wiring on a surface of the stem portion,
 wherein a control chip is directly, electrically, connected to solder bump on the upper horizontal crossbar, wherein the control chip is disposed parallel to the upper surface of the base portion.

12. The shank structure of claim 11, wherein the shank structure is disposed in a comb of shanks.

13. The shank structure of claim 11, further comprising a first sub-shank and a second sub-shank, each comprising a set of the plurality of sensing elements disposed on a first side thereof, and second sides of the first sub-shank and the second sub-shank are bonded directly to one-another by an adhesive such that the plurality of sensing elements of the shank structure are on the first sides of the first sub-shank and the second sub-shank and one of the first sides of the first sub-shank forms the surface of the stem portion and another one of the first sides of the first sub-shank forms an opposite surface of the stem portion of the shank structure.

14. The shank structure of claim 11, further comprising a plurality of nano-patterned features comprising non-random topography disposed on the plurality of sensing elements.

15. The shank structure of claim 11, further comprising a biological functionalization material disposed on exposed surfaces of the plurality of sensing elements.

16. The shank structure of claim 11, wherein the base portion comprises:
 a processor; and
 a memory.

* * * * *